(12) United States Patent
Nabutovsky et al.

(10) Patent No.: US 9,364,170 B2
(45) Date of Patent: Jun. 14, 2016

(54) METHOD AND SYSTEM TO CHARACTERIZE MOTION DATA BASED ON NEIGHBORING MAP POINTS

(71) Applicant: Pacesetter Inc., Sunnyvale, CA (US)

(72) Inventors: Yelena Nabutovsky, Mt. View, CA (US); Hoda Razavi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 78 days.

(21) Appl. No.: 14/270,181

(22) Filed: May 5, 2014

(65) Prior Publication Data

US 2015/0313511 A1    Nov. 5, 2015

(51) Int. Cl.
*A61B 5/04*      (2006.01)
*A61B 5/11*      (2006.01)
*A61B 5/042*     (2006.01)
*A61B 5/06*      (2006.01)
*A61B 5/00*      (2006.01)

(52) U.S. Cl.
CPC ............... *A61B 5/1126* (2013.01); *A61B 5/042* (2013.01); *A61B 5/061* (2013.01); *A61B 5/1102* (2013.01); *A61B 5/6869* (2013.01); *A61B 5/7278* (2013.01); *A61B 5/0422* (2013.01); *A61B 5/062* (2013.01); *A61B 5/1107* (2013.01); *A61B 5/7289* (2013.01)

(58) Field of Classification Search
None
See application file for complete search history.

(56) References Cited

U.S. PATENT DOCUMENTS

| | | |
|---|---|---|
| 5,391,199 A | 2/1995 | Ben-Haim |
| 6,233,476 B1 | 5/2001 | Strommer et al. |
| 6,301,496 B1 | 10/2001 | Reisfeld |
| 6,609,027 B2 | 8/2003 | Kroll et al. |
| 6,633,686 B1 | 10/2003 | Bakircioglu et al. |
| 6,728,562 B1 | 4/2004 | Budd et al. |
| 6,751,492 B2 | 6/2004 | Ben-Haim |
| 6,978,168 B2 | 12/2005 | Beatty et al. |
| 7,197,354 B2 | 3/2007 | Sobe |
| 7,263,297 B2 | 8/2007 | Verbana |
| 7,276,064 B2 | 10/2007 | Paul et al. |

(Continued)

FOREIGN PATENT DOCUMENTS

| | | |
|---|---|---|
| EP | 1 070 480 A2 | 1/2001 |
| EP | 1 508 300 A1 | 2/2005 |

(Continued)

OTHER PUBLICATIONS

Notice of Allowance mailed Jun. 22, 2015; Related U.S. Appl. No. 14/328,523.

(Continued)

*Primary Examiner* — Brian T Gedeon
*Assistant Examiner* — Ankit D Tejani
(74) *Attorney, Agent, or Firm* — Theresa A. Raymer

(57) ABSTRACT

A method and system are provided for characterizing motion data. The method and system obtain point specific (PS) motion data for a plurality of map points. The PS motion data indicates an amount of motion that occurred at the corresponding map point on a wall of the heart during at least one cardiac cycle. The method and system, calculate mechanical activation times (MAT) for the map points, identifying a group of neighbor map points for a current map point, and modifying the MAT corresponding to the current map point based on the MATs corresponding to at least a portion of the group of neighboring map points. Further, the method and system repeat the identifying and modifying operations for at least a subset of the map points.

20 Claims, 9 Drawing Sheets

(56) References Cited

U.S. PATENT DOCUMENTS

| | | | |
|---|---|---|---|
| 7,338,486 B2 | 3/2008 | Sliwa et al. | |
| 7,386,339 B2 | 6/2008 | Strommer et al. | |
| 7,505,809 B2 | 3/2009 | Strommer et al. | |
| 7,697,973 B2 | 4/2010 | Strommer et al. | |
| 7,881,769 B2 | 2/2011 | Sobe | |
| 8,016,764 B1 | 9/2011 | Shelchuk | |
| 2003/0093067 A1 | 5/2003 | Panescu | |
| 2003/0233039 A1 | 12/2003 | Shao et al. | |
| 2005/0154282 A1 | 7/2005 | Li et al. | |
| 2006/0245536 A1* | 11/2006 | Boing | A61B 6/032 378/8 |
| 2007/0073179 A1 | 3/2007 | Afonso et al. | |
| 2007/0100332 A1 | 5/2007 | Paul et al. | |
| 2007/0106146 A1 | 5/2007 | Altmann et al. | |
| 2007/0181139 A1 | 8/2007 | Hauck | |
| 2007/0244479 A1 | 10/2007 | Beatty et al. | |
| 2007/0270705 A1 | 11/2007 | Starks | |
| 2008/0009758 A1 | 1/2008 | Voth | |
| 2008/0091193 A1 | 4/2008 | Kauphusman et al. | |
| 2009/0163904 A1 | 6/2009 | Miller et al. | |
| 2009/0171345 A1 | 7/2009 | Miller et al. | |
| 2010/0168550 A1 | 7/2010 | Byrd et al. | |
| 2010/0268059 A1* | 10/2010 | Ryu | A61B 5/042 600/407 |
| 2011/0243401 A1 | 10/2011 | Zabair et al. | |
| 2012/0184863 A1 | 7/2012 | Harlev et al. | |
| 2013/0222415 A1 | 8/2013 | Vilsmeier | |
| 2013/0272592 A1 | 10/2013 | Eichler et al. | |
| 2015/0045867 A1 | 2/2015 | Krishnan et al. | |
| 2015/0133802 A1 | 5/2015 | Nabutovsky et al. | |
| 2015/0141765 A1 | 5/2015 | Razavi et al. | |
| 2015/0141858 A1 | 5/2015 | Razavi et al. | |

FOREIGN PATENT DOCUMENTS

| | | |
|---|---|---|
| EP | 2 757 528 A1 | 7/2014 |
| WO | 97/24981 A2 | 7/1997 |
| WO | 2012/090148 A1 | 7/2012 |

OTHER PUBLICATIONS

Bogatyrenko, Evgeniya et al., Efficient Physics-Based Tracking of Heart Surface Motion for Beating Heart Surgery Robotic Systems, International Journal of Computer Assisted Radiology and Surgery, vol. 6, No. 3, pp. 387-399, Aug. 2010.

International Search Report and Written Opinion in PCT Application No. PCT/US2015/028206 (Jul. 22, 2015).

Quatember, Bernhard et al., "Geometric Modeling and Motion Analysis of the Epicardial Surface of the Heart", Mathematics and Computers in Simulation, vol. 81, No. 3, pp. 608-622, Nov. 2010.

Segars, W. Paul et al., "A Realistic Spline-Based Dynamic Heart Phantom", IEEE Transactions on Nuclear Science, vol. 46, No. 3, pp. 503-506, Jun. 1999.

U.S. Appl. No. 09/107,731, filed Jun. 30, 1998 for "Chamber Mapping System".

Advisory Action mailed Aug. 10, 2015; Related U.S. Appl. No. 12/347,216.

Amendment filed Jun. 25, 2015; Related U.S. Appl. No. 12/347,216.

Final Office Action mailed May 4, 2015; Related U.S. Appl. No. 12/347,216.

Amendment filed Dec. 18, 2014; Related U.S. Appl. No. 12/347,216.

Non-Final Office Action mailed Oct. 2, 2014; Related U.S. Appl. No. 12/347,216.

Advisory Action mailed May 1, 2014; Related U.S. Appl. No. 12/347,216.

Amendment filed Apr. 24, 2014; Related U.S. Appl. No. 12/347,216.

Applicant Interview Summary, Apr. 21, 2014; Related U.S. Appl. No. 12/347,216.

Final Office Action mailed Feb. 25, 2014; Related U.S. Appl. No. 12/347,216.

Amendment filed Feb. 4, 2014; Related U.S. Appl. No. 12/347,216.

Non-Final Office Action mailed Nov. 21, 2013; Related U.S. Appl. No. 12/347,216.

Amendment filed Oct. 29, 2012; Related U.S. Appl. No. 12/347,216.

Advisory Action mailed Oct. 11, 2012; Related U.S. Appl. No. 12/347,216.

Amendment filed Oct. 1, 2012; Related U.S. Appl. No. 12/347,216.

Advisory Action mailed Sep. 12, 2012; Related U.S. Appl. No. 12/347,216.

Amendment filed Aug. 28, 2012; Related U.S. Appl. No. 12/347,216.

Final Office Action mailed Jun. 29, 2012; Related U.S. Appl. No. 12/347,216.

Amendment filed May 14, 2012; Related U.S. Appl. No. 12/347,216.

Interview Summary, Feb. 28, 2012; Related U.S. Appl. No. 12/347,216.

Non-Final Office Action mailed Feb. 13, 2012; Related U.S. Appl. No. 12/347,216.

Non-Final Office Action mailed Dec. 11, 2015; Related U.S. Appl. No. 14/703,460.

Notice of Allowance mailed Dec. 8, 2015; Related U.S. Appl. No. 12/347,216.

Notice of Allowance mailed Oct. 27, 2015; Related U.S. Appl. No. 14/328,523.

Final Office Action mailed Jan. 22, 2016; Related U.S. Appl. No. 14/270,176.

* cited by examiner

METHOD AND SYSTEM TO CHARACTERIZE MOTION DATA BASED ON NEIGHBORING MAP POINTS

RELATED APPLICATION DATA

The present application is related to the following applications: U.S. provisional application Ser. No. 61/906,311, filed Nov. 19, 2013, titled "METHOD AND SYSTEM TO ASSESS MECHANICAL DYSSYNCHRONY BASED ON MOTION DATA COLLECTED BY A NAVIGATION SYSTEM", U.S. provisional application Ser. No. 61/910,630, filed Nov. 19, 2013, titled "METHOD TO MEASURE CARDIAC MOTION USING A CARDIOVASCULAR NAVIGATION SYSTEM", U.S. provisional application Ser. No. 61/906,305, filed Nov. 19, 2013, titled "METHOD TO IDENTIFY CARDIAC CYCLES WITH CONSISTENT ELECTRICAL RHYTHM AND MECHANICAL BEHAVIOR FOR COMPILATION INTO A REPRESENTATIVE CHARACTERIZATION OF CARDIAC MOTION", U.S. application Ser. No. 14/270,186, titled "METHOD AND SYSTEM FOR CALCULATING STRAIN FROM CHARACTERIZATION DATA OF A CARDIAC CHAMBER", filed on May 5, 2014, U.S. application Ser. No. 14/270,176, titled "METHOD AND SYSTEM FOR DISPLAYING A THREE DIMENSIONAL VISUALIZATION OF CARDIAC MOTION", filed on May 5, 2014, and U.S. application Ser. No. 14/270,191, titled "METHOD AND SYSTEM TO AUTOMATICALLY ASSIGN MAP POINTS TO ANATOMICAL SEGMENTS", filed on May 5, 2014, all of which are expressly incorporated herein by reference in their entirety.

BACKGROUND OF THE INVENTION

Embodiments of the present invention generally relate to methods and systems for cardiovascular navigation, and more particularly for characterizing motion in a cardiac chamber or organ.

Cardiovascular navigation systems (CNS) provide real-time position and orientation information in relation to a part of the cardiovascular system, such as, the heart based on sensors placed at various locations within the cardiovascular system. The CNS may be integrated with a fluoroscopic (or other diagnostic) imaging system and track the sensors continuously within an imaging volume defined by the fluoroscopic system, on both live and recorded background diagnostic images.

Recently, it has been proposed to utilize the CNS to evaluate the motion of the heart and identify a desired (e.g., optimal) location for placement of a left ventricular (LV) lead. For example, the CNS may systematically record information, such as displacement of the sensors, associated with various endocardial and epicardial locations of the LV. Depending on the size of the heart and other factors during the procedure, there may be between 40 and 120 endocardial LV locations and up to 10 epicardial locations at which the CNS obtains recordings for each patient.

Systems have been proposed to characterize the motion of the heart, based on mechanical activation that is determined from sensor information at various endocardial and epicardial locations. The mechanical activation is used to measure the maximum extent of motion of the heart. However, the sensor information may include a complex pattern with multiple displacement apexes or peaks making determination of the mechanical activation point difficult. A need exists for improved methods and systems that utilize cardiovascular navigation systems for characterizing motion data having complex patterns.

SUMMARY

In accordance with an embodiment herein, a method is provided for characterizing motion data. The method includes obtaining point specific (PS) motion data for a plurality of map points. The PS motion data indicates an amount of motion that occurred at the corresponding map point on a wall of the heart during at least one cardiac cycle. The method also includes, calculating mechanical activation times (MAT) for the map points, identifying a group of neighbor map points for a current map point, and modifying the MAT corresponding to the current map point based on the MATs corresponding to at least a portion of the group of neighboring map points. Further, the method repeats the identifying and modifying operations for at least a subset of the map points.

Optionally, the PS motion data defines a motion waveform at the corresponding map point. The motion waveform represent displacement over a select period of time, such that, the calculating operation above that calculates the MATs is based on the motion waveforms. Further, the method may include assigning clarity scores to each of the motion waveforms based on a distinctiveness of a feature of interest within the motion waveforms used to determine the MATs. The clarity scores represent confidence levels in the corresponding MATs.

In an embodiment, a system for characterizing motion data collected by cardiovascular navigation system (CNS). The system including a plurality of physiological sensors. The physiological sensors are positioned adjacent to a plurality of map points and acquire point specific (PS) motion data at corresponding map points. The PS motion data indicates an amount of motion that occurred at the map points on a wall of the heart during at least one cardiac cycle. The system includes a PS motion data analysis circuit module. The PS motion data analysis circuit module is configured to determine, from the map points, a mechanical activation time (MAT). Further, the system includes a MAT modification circuit module. The MAT modification circuit module is configured to modify the MAT of a selected map point based on the MATs corresponding to at least a subset of the map points.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

The methods herein may be implemented as a software algorithm, package, or system that directs one or more hardware circuits or circuitry to perform the actions described herein. For example, the operations of the methods herein may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

At least one technical effect of at least one portion of the methods and systems described herein is at least (i) obtaining point specific (PS) motion data for a plurality of map points, (ii) calculating mechanical activation times (MAT) for the map points, (iii) identifying a group of neighboring map points at least partially surrounding a current map point, (iv) modifying the MAT corresponding to the current map point based on MATs corresponding to at least a portion of the group of neighboring map points, and (v) repeat the identifying and modifying operations for at least a subset of the map points thereby deriving updated MAT's based on neighboring MAT's.

Figure 1:
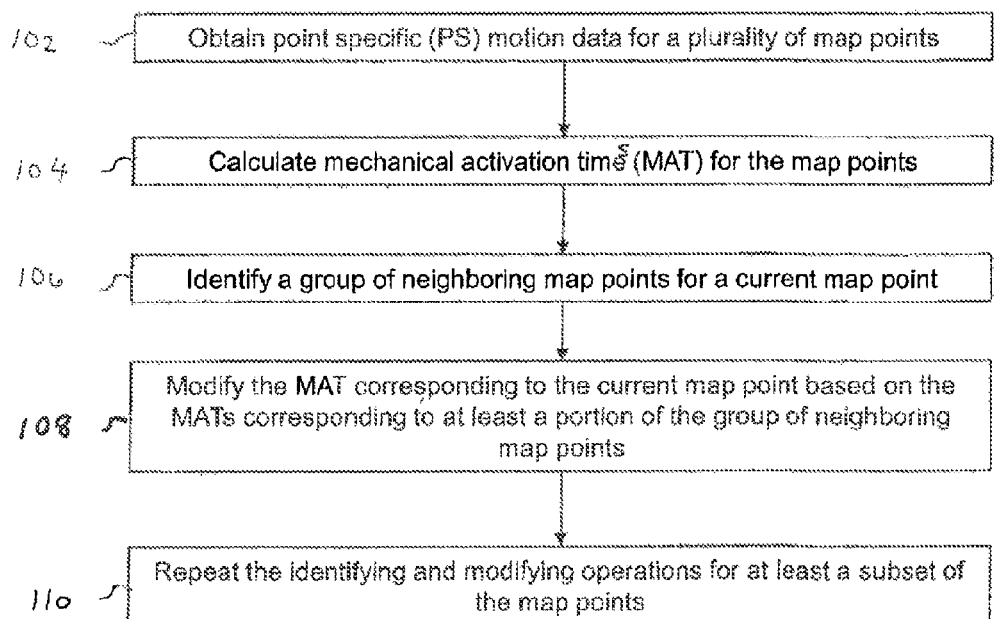
FIG. 1 illustrates a flow chart of a method for characterizing motion data collected by a cardiovascular navigation system, in accordance with an embodiment herein.

FIG. 1 illustrates a flowchart of a method 100 for characterizing motion data collected by a cardiovascular navigation system (CNS). The method 100, for example, may employ structures or aspects of various embodiments (e.g., systems and/or methods) discussed herein (e.g., the CNS 210 in FIG. 2). In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Furthermore, it is noted that the following is just one possible method of characterizing motion data collected by the CNS. It should be noted, other methods may be used, in accordance with an embodiment herein.

Beginning at 102, the method obtains point specific (PS) motion data for a plurality of map points. The PS motion data may be acquired or collected using a cardiovascular navigation system (CNS) 210 with an electrophysiological sensor 252 in real-time or prior to implementation of FIG. 1. At 104, the method 100 calculates mechanical activation times (MAT) for the map points. At 106, the method 100 identifies a group of neighboring map points (e.g. the map points) for a current map point (e.g., the map point). At 108, the method 100 modifies an MAT corresponding to a current map point based on the calculated MATs corresponding to at least a portion of the group of neighboring map points. At 110, the method 100 repeats the identifying and modifying operations for at least a subset of the map points (e.g., the map point). For example, an alternative current map point is selected and the operation at 106 and 108 is repeated with the alternative current map point. Next, the method of FIG. 1 is discussed in more detail in connection with FIGS. 2-10.

Figure 2:
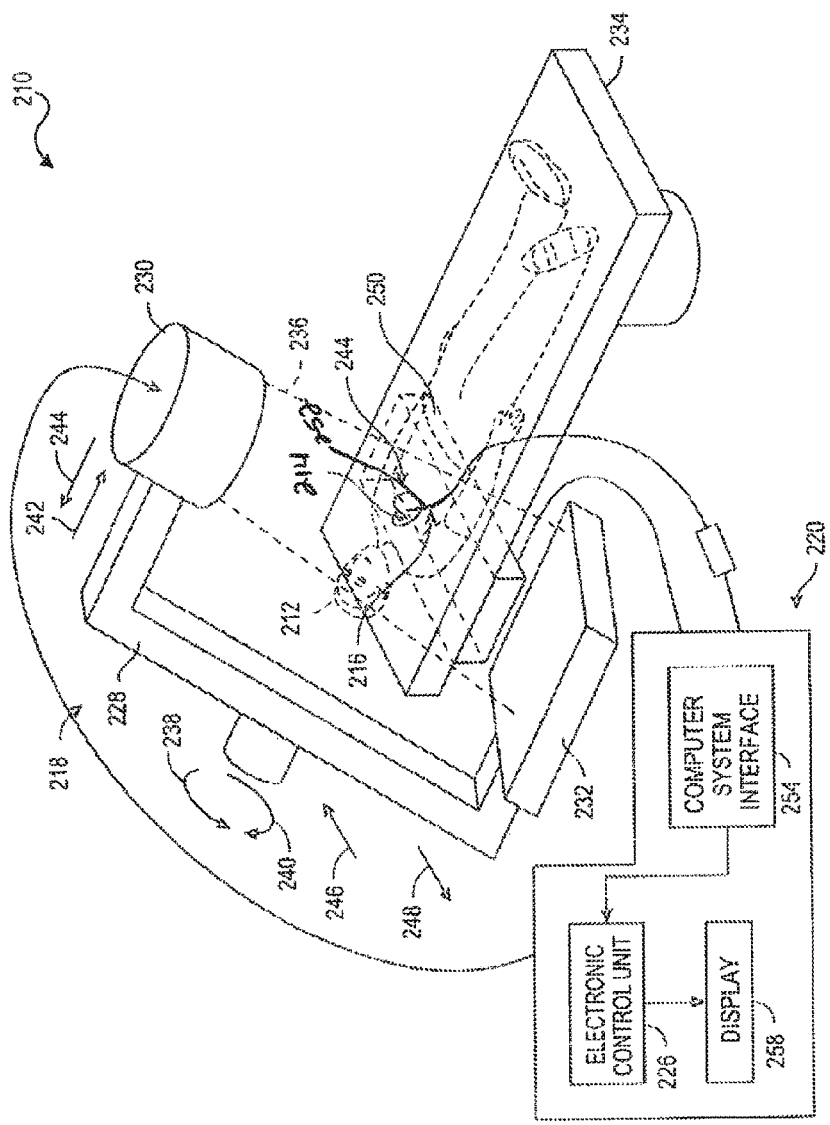
FIG. 2 illustrates a cardiovascular navigation system for use in imaging an anatomical region of the heart and to collect motion data, in accordance with an embodiment herein.

FIG. 2 illustrates a cardiovascular navigation system (CNS) 210, of an embodiment, for use in imaging an anatomical region of a patient 212, such as, a heart 214. A medical tool 216 is placed within the anatomical region, such as for example, an electrophysiological (EP) mapping catheter or a catheter generally described or shown in U.S. Pat. No. 7,881,769, which is expressly incorporated herein by reference. The medical tool 216 includes a plurality of electrophysiological sensors 252 that may be placed on the endocardial or epicardial surface of the left ventricle (LV) of the heart 214. The electrophysiological sensors 252 may be attached to the distal or proximal end of the medical tool 216, or any point in between. The electrophysiological sensors 252 measure a position and an electrical potential or an electric current of biological cells and tissues. The electrophysiological sensors 252 transmits the position and electrical potential information to an electronic control unit (ECU) 226. For example, the electrophysiological sensors 252 may be positioned by the medical tool 216 to measure PS motion data for a plurality of map points of the wall of the heart 214. It should be understood, however, that the electrophysiological sensors 252 could be used in a variety of anatomical regions or alternative map points within the heart 214 or other organs in which motion characterization may be of interest. Additionally or alternatively, the electrophysiological sensors 252 may be replaced by separate motion sensors and electrical sensors. The motion sensors in contact with the region of interest (e.g., the LV of the heart 214) measuring the position sensors as well as the electrical sensors that are measuring the PS motion data of the region of interest. Optionally, the ECU 226 may receive the PS motion data and electrical sensor measurements simultaneously from the motion sensors and electrical sensors.

A navigation system 220 is provided to determine the position and orientation of the medical tool 216 within the body of the patient 212. In the illustrated embodiment, the navigation system 220 comprises a magnetic navigation system in which magnetic fields are generated in the anatomical region and position sensors associated with the medical tool 216 generate an output that is responsive to the position of the sensors within the magnetic field. The navigation system 220 may comprise, for example, the systems generally shown and described in, for example, U.S. Pat. Nos. 6,233,476, 7,197, 354, 7,386,339, and 7,505,809 all of which are expressly incorporated by reference in their entirety. Although a magnetic navigation system is shown in the illustrated embodiment, it should be understood that the embodiments could find use with a variety of navigation systems including those based on the creation and detection of axes specific electric fields. The navigation system 220 may include a transmitter assembly 250.

The transmitter assembly 250 may include a plurality of coils arranged orthogonally to one another to produce a magnetic field in and/or around the anatomical region of interest. It should be noted that, although the transmitter assembly 250 is shown under the body of the patient 212 and under the table 234 in FIG. 2, the transmitter assembly 250 may be placed in another location, such as, attached to the radiation emitter 230, from which the magnetic field generators can project a magnetic field in the anatomical region of interest. In accordance with certain embodiments the transmitter assembly 250 is within the field of view 236. The ECU 226 may control the generation of magnetic fields by transmitter assembly 250.

The electrophysiological sensors 252 are configured to generate an output dependent on the relative position of electrophysiological sensors 252 within the field generated by the transmitter assembly 250. In FIG. 2, the electrophysiological sensor 252 and the medical tool 216 are shown disposed around the heart 214. The navigation system 220 determines the location of the electrophysiological sensors 252 within the generated field, and thus the position of the medical tool 216 as well. The navigation system 220 may further determine navigation coordinates, such as a Cartesian coordinate (e.g., (X, Y, Z), of the navigation coordinate system.

The ECU 226 of the navigation system 220 may include or represent hardware circuits or circuitry that include and/or are connected with one or more logic based devices, such as processors, microprocessors, controllers, microcontrollers, or other logic based devices (and/or associated hardware, circuitry, and/or software stored on a tangible and non-transitory computer readable medium or memory). The ECU 226 may receive a plurality of input signals including signals generated by the medical tool 216, the electrophysiological sensors 252, an operator system interface 254, and one or more patient reference sensors (not shown) and generate a plurality of output signals including those used to control the medical tool 216 and/or the display 258. The ECU 226 may also receive an input signal from an organ monitor (not shown), such as an ECG monitor, and sort or segregate images from an imaging system 218 based on a timing signal of a monitored organ. For example, ECU 226 may sort images based on the phase of the patient's cardiac cycle at which each image was collected, as more fully described in U.S. Pat. No. 7,697,973, which is hereby incorporated by reference in its entirety.

The ECU 226 may acquire measurements from the electrophysiological sensors 252 of PS motion data indicating an amount of motion that occurred at the corresponding map point on a wall of the heart 214 during at least one cardiac cycle. The heart may be divided into numerous map points along the was of the various chambers.

Figure 3:
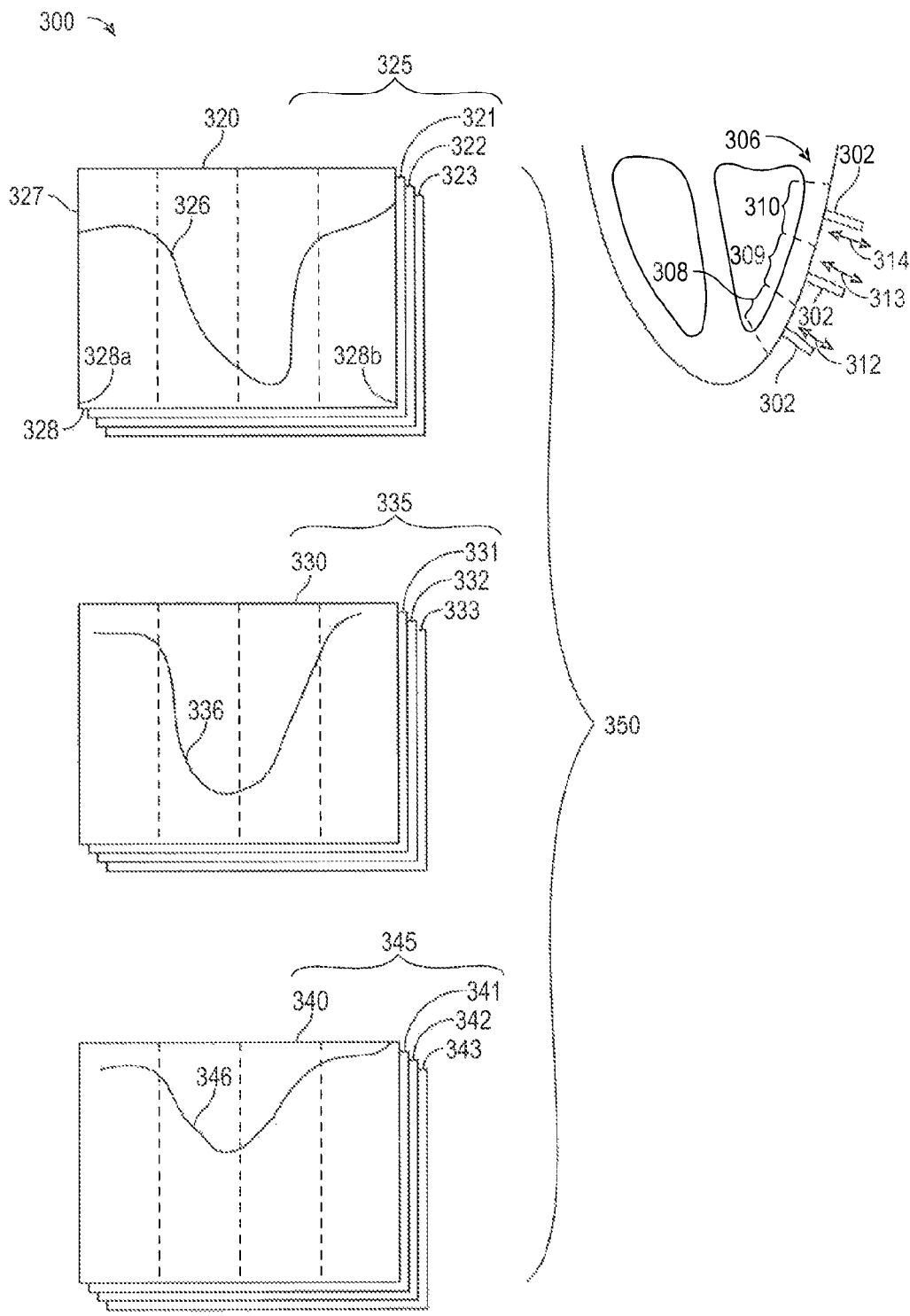
FIG. 3 illustrates a graphical representation of a plurality of map points of a heart.

FIG. 3 illustrates a graphical representation of a plurality of map points associated with a portion of a heart 300, such as heart wall 306, for which it is desirable to measure PS motion data. The term "point specific" is used to indicate that the motion data is associated with a single select location on the heart wall. The data values represent positions of the single select location over one or more cardiac cycles. The heart wall 306 may be separated into map points 308-310. The example of FIG. 3 shows three map points of interest 308-310 along the wall of the LV. Optionally, more or fewer map points of interest may be designated. A tool 302 (e.g., the medical tool 216 with the plurality of electrophysiology sensors 252) is positioned directly against the heart wall 306 at one or more points within each map point of interest 308-310. The tool 302 measures movement of the one or more points over a select period of time. In the example of FIG. 3, the tool 302 is shown positioned against a point of interest in each map point 308-310 at different points in time.

For example, the tool 302 is positioned, during a first measuring operation, at a point within the map point 308 while collecting PS motion data associated with movement (e.g., along the arrow 312) by the map point 308. The movement may be in various linear, transverse, or rotational directions. Next, the tool 302 may be positioned, during a second measuring operation, at a point within the map point 309 while collecting PS motion data associated with movement (e.g., along the arrow 313) by the map point 309. Next, the tool 302 is positioned, during a third measuring operation, at a point within the map point 310 while collecting PS motion data associated with movement (e.g., along the arrow 314) by the map point 310.

The position of the tool 302 may be continuously monitored by a navigation system (e.g., the navigation system 220) to obtain sets of motion data associated with each map point 308-310 over a select period of time, such as, during at least one cardiac cycle. In FIG. 3, a motion waveform subset 320 is collected during one cardiac cycle while the tool 302 is held against the LV wall acquiring PS motion data for a point within the map point 308. The PS motion data may define a motion waveform 326 at the map point 308. The motion waveform 326 represents a displacement of the map point 308, illustrated with respect to a vertical axis 327 axis representing an amount of displacement of the map point 308 from a start reference position, during the cardiac cycle, illustrated along a horizontal axis 328 representing time from a beginning 328a to an end 326b of the cardiac cycle. Optionally, the tool 302 may be held against the LV wall at a point within the map point 308 for multiple heart beats or cardiac cycles thereby generating multiple motion waveform subsets 320-323 (e.g., for four consecutive heart beats). Optionally, the PS motion data subsets 320-323 may be collected for fewer than or more than four heart beats. The PS motion data subsets 320-323 associated with the map point 308 may be grouped to form a collection 325 of motion waveform subsets 320-323 associated with a single map point 308.

Additionally or alternatively, the motion waveform 326 of the PS motion at the map point 308 may represent a waveform indicative of strain (e.g., tissue deformation) or strain rate at the map point 308 from the beginning 328a to the end 328b of the cardiac cycle, traversing along an axis formed by longitudinal divisions 742 (FIG. 7)), a radial direction, and/or a circumferential direction (e.g., traversing along an axis formed by circumferential divisions 740 (FIG. 7)). Strain rate is the rate at which the tissue deformation or strain occurs over time. Strain rate may be measured as the difference, in velocity between two map points (e.g., toward each other, away from each other) along the heart wall, normalized to the distance between the two map points.

For example, the ECU 226 may set a position reference point at the beginning 328a of the cardiac cycle. During the cardiac cycle, the ECU 226 may compare instantaneous positions of the tool 302 at the map point 308, over the cardiac cycle, against the positions of surrounding map points to acquire the PS motion data representing strain of the map point 308. The PS motion data may define the strain over the cardiac cycle. Optionally, the ECU 226 may determine the strain rate of the map point 308 by calculating the derivative or change in the strain over time. The strain or strain rate at a select map point may be relative to one or more other map points. Optionally, the select map point may have multiple strains or strain rates associated there with.

Once a desired amount of motion data is collected for the map point 308, the tool 302 is moved to a next desired position, such as at a point within the map point 309. Next, the data collection process is repeated to obtain PS motion data forming a motion waveform 336 indicative of an amount of motion experienced or displacement of the map point 309 over a cardiac cycle (e.g., heart beat). Optionally, the tool 302 may be held for multiple heart beats to obtain PS motion data subsets 330-333 over a corresponding number of heart beats (e.g., cardiac cycles).

Once a desired amount of motion data is collected for the map point 309, the tool 302 is moved to a next desired position such as at a point within the map point 310. Next, the data collection process is repeated to obtain PS motion data forming a motion waveform 346 indicative of an amount of motion experienced or a displacement of the map point 310 over a cardiac cycle (e.g., heart beat). Optionally, the tool 302 may be held for multiple heart beats to obtain PS motion data subsets 340-343 over a corresponding number of heart beats (e.g., cardiac cycles). The motion waveform subsets 330-333, and 340-343, which are associated with map points 309 and 310, may be grouped to form collections 335 and 345, respectively, associated with single map points 309 and 310. The plurality of motion waveform subsets 320-343 for all map points 308-310 of interest of the heart wall 306 may collectively define a motion data set 350.

Optionally, more map points of the heart wall 306 may be studied to collect additional motion waveform subsets of motion data. For example, the walls of the right ventricular, right atrium, and/or left atrium may also be divided into map points, for which motion data is collected.

A cardiovascular navigation system (e.g., CNS 110) collects the motion data from one or more tools 302. The motion data 350 may be analyzed to identify and remove non-ectopic beats and to eliminate beats with abrupt mechanical movement. Optionally, the motion data 350 may include averages of motion data collected over multiple heart beats (cardiac cycles). For example, the motion waveform subsets 320-323 may be combined through averaging or otherwise. Optionally, the motion data 350, which is utilized in connection with embodiments described hereafter, may include information indicative of a radial component of wall movement, and/or may include information indicative of a longitudinal component of wall movement. Optionally, the motion data may include information associated with 3-dimensional (3-D) movement calculated as a 3-D distance from an initial position at a select starting point in the cardiac cycle, such as an R-wave or local electrical activation time.

Optionally, the CNS 110 may adjust the motion waveform subsets 325, 335, 345 to extend over a common time interval. For example, the motion waveform subsets 325, 335, 345 may be temporally equalized by "stretching" the motion waveforms that have shorter cycle lengths until the shorter motion waveform subsets have a length equal to the predetermined interval. The common time interval may be predetermined, or automatically selected, such as by choosing a length corresponding to the longest, shortest, or average length of the motion waveform subset 320-323. The time interval may be set to begin at a point in time defined by a global signal such as the peak of the R-wave as detected by using the Electrocardiogram (ECG) or Intracardiac Electrogram (IEGM) signals as described in the provisional application titled "METHOD TO MEASURE CARDIAC MOTION USING A CARDIOVASCULAR NAVIGATION SYSTEM,", U.S. Provisional Application Ser. No. 61/906,300, which is expressly incorporated herein by reference in its entirety. Optionally, the time interval may be defined to begin based on another global marker of electrical activity (e.g., the T-wave, P-wave).

Figure 4:
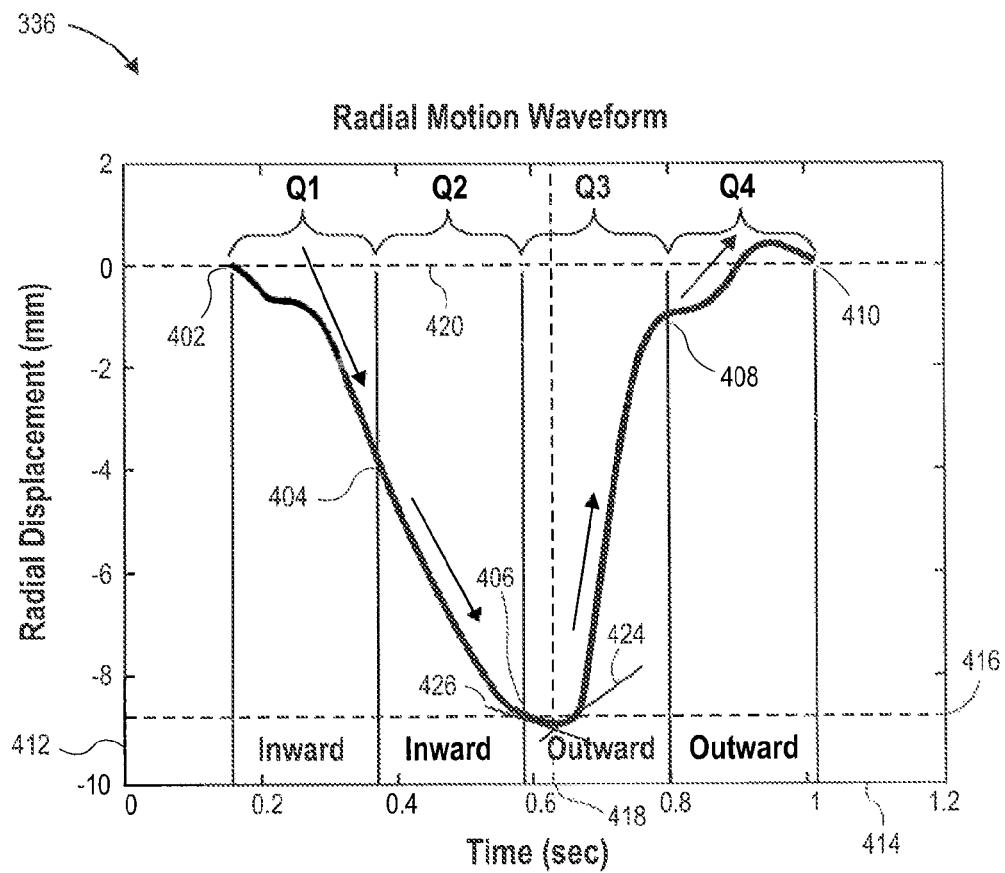
FIG. 4 illustrates a motion waveform associated with one wall map point and collected during a single cardiac cycle, in accordance with an embodiment herein.

Returning to FIG. 1, at 104, the method 100 calculates mechanical activation times (MAT) for the map points 308-310. FIG. 4 illustrates an expanded view of the motion waveform 336 associated with the map point 309 and collected during a single cardiac cycle (e.g., heart beat). The motion waveform 336 plots radial displacement (e.g., in millimeters) of the map point of interest along a vertical axis 412 and time along a horizontal axis 414. The direction of movement is illustrated from a beginning/zero point in time until completion of a cardiac cycle (e.g., after 1 sec.). The motion waveform 336 is divided into sectors Q1-Q4 that are associated with portions or phases of the cardiac cycle. The motion waveform 336 exhibits an amount of radial motion during each sector Q1-Q4.

The ECU 226 may determine a magnitude and/or direction of radial motion corresponding to the map point (e.g., the map point 308, 309, 310) of the wall of the heart during the associated phases of the cardiac cycle. The radial motion may be quantified in terms of the direction of motion and/or the amplitude/magnitude of motion. Optionally, motion may occur in directions other than radially. With reference to FIG. 4, the motion may be determined by finding net movement during the sector Q1, Q2, Q3 or Q4. For example, in sector Q1 the net movement is determined by identifying a location (displacement) of the first point 402 in the sector Q1 and identifying a location of the last point 404 in the sector Q1. The points 402-410 represent sector transition points and can be compared to determine the net movement. For example, in sector Q3, the net movement is approximately 8 mm, as the wall map point moved from a radial displacement of −9.0 at the beginning of sector Q3 to a radial displacement of −1.0 at the end of sector Q3 (corresponding to the beginning of sector Q4).

Further, the ECU 226 may determine the MAT for the map point 309 based on the change in direction of motion and/or the amplitude/magnitude of motion of the waveform. The MAT may represent a point in time when the wall of the heart, measured at the map point, transitions from a systole to diastole stage. During the transition, the displacement of the map point may shift from a radially inward direction that is away from the electrophysiological sensor 252 to a radially outward direction that is towards the direction of the electrophysiological sensor 252. Optionally, a time of the transition may be determined by correlating the electrical information of the heart measured by the ECG monitor to the mechanical information measured by the electrophysiological sensors 252. The ECU 226 may determine the MAT as a time at which the electrical information from the ECG monitor that correlates to the systole to diastole transition of the wall at the map point.

Additionally or alternatively, the MAT for the map point 309 may represent a time when the motion waveform 336 reaches a minimum displacement along the vertical axis 412. For example, the motion waveform 336 reached the minimum displacement along the vertical axis 412, within sector Q3, at a displacement 412 and time 418. The ECU 226 may determine that the MAT to be at the time 418 representing the time when the minimum displacement, the displacement 412, occurred.

Optionally, the MAT for the map point 309 may represent a time when the motion waveform 336 is at a maximum displacement from a predetermined reference line 420. For example, the ECU 226 may have the predetermined reference line 420. The predetermined reference line 420 maybe set by a user of the CNS 210 using the operator system interface 254. Optionally, the predetermined reference line 420 may be set at the displacement of the sector transition point 402 or 410. The ECU 226 may calculate the displacement of the PS motion data points along the motion waveform 336 from the predetermined reference line 420 and select the PS motion data point that has the greatest or maximum displacement relative to the remaining PS motion data point from the predetermined reference line 420. The ECU 226 may select the PS motion data point occurring at the time 418, and designate the time 418 as the MAT for the map point 309.

Optionally, the MAT of the map point 309 may represent a time when the motion waveform 336 has an initial deviation towards a baseline 416 representing the onset of an opposing motion. The ECU 226 may set the baseline 416 at a sector transition point located between sectors with opposing net movements, which would indicate the opposing motion of the map point 309. For example, Q2 has an inward net movement and is adjacent to Q3 that has an outward net movement. The ECU 226 may select the displacement of the transition point 406, which is between Q2 and Q3, as the baseline 416. The ECU 226 may compare the displacement of each PS motion data points with adjacent PS motion data points below the baseline 416 to determine the time of a PS motion data point with lower distance indicating movement towards the baseline 416 and may be determined as the MAT.

Additionally or alternatively, the ECU 226 may calculate slopes or gradients of the PS motion data point. A zero slope or opposing slopes from two sets of adjacent PS motion data points may indicate the onset of an opposing motion, which may be used to calculate the MAT for the map point. For example, the ECU 226 may calculate slopes traversing along the horizontal axis 414 from continuous sets of adjacent PS motion data points that are below the baseline 416. The ECU 226 may calculate a negative slope 426 and a positive slope 424 from two adjacent sets of PS motion data points that are below the baseline 416. The ECU 226 may calculate that the MAT is the time point between the two adjacent sets of PS motion data points or the time point that is located at the intersection of the positive and negative slopes 424 and 426.

Optionally, the ECU 226 may determine an extent of motion (EM) of the map points from the PS motion data forming the motion waveform. The EM may represent the maximum extent of motion of the map point. The EM may be calculated based on a comparison of the maximum and minimum displacements of the PS motion data at the map point.

In an embodiment, the ECU 226 may assign a clarity score to the motion waveform based on a distinctiveness of a feature of interest within the motion waveform. The clarity score represents a level of confidence that a MAT value is correct. The confidence (and clarity score) increases or decreases based on a shape of the motion wave form, and thus the distinctiveness of the feature of interest. The distinctive feature of interest may represent a region of the motion waveform used to determine the MAT of the map point. For example, the distinctive feature may represent a peak or vertex of the motion waveform having a U-shape or parabolic shape. Optionally, the clarity score may be associated with both the MAT and EM at the corresponding map point. Additionally or alternatively, the distinctive feature of interest may be a line symmetry of the motion waveform such that the motion waveform has at most two PS motion data points at a common level of displacement. Optionally, the distinctive feature may be based on the slopes of the PS motion data points within the motion waveform.

Deviations from the distinctive feature may indicate unclear motion waveform morphology that may be caused by errors in the acquired PS motion data for the map point that defines the motion waveform. For example, if the electro-physiological sensor 252 is not directly against the heart wall during the entire cardiac cycle the motion waveform may have a flat peak, multiple peaks, lack of line symmetry, or the like. The ECU 226, for example, may detect or identify the deviations from the distinctive feature and designate a lower confidence of the calculated MAT by with a corresponding clarity score.

Figure 5:
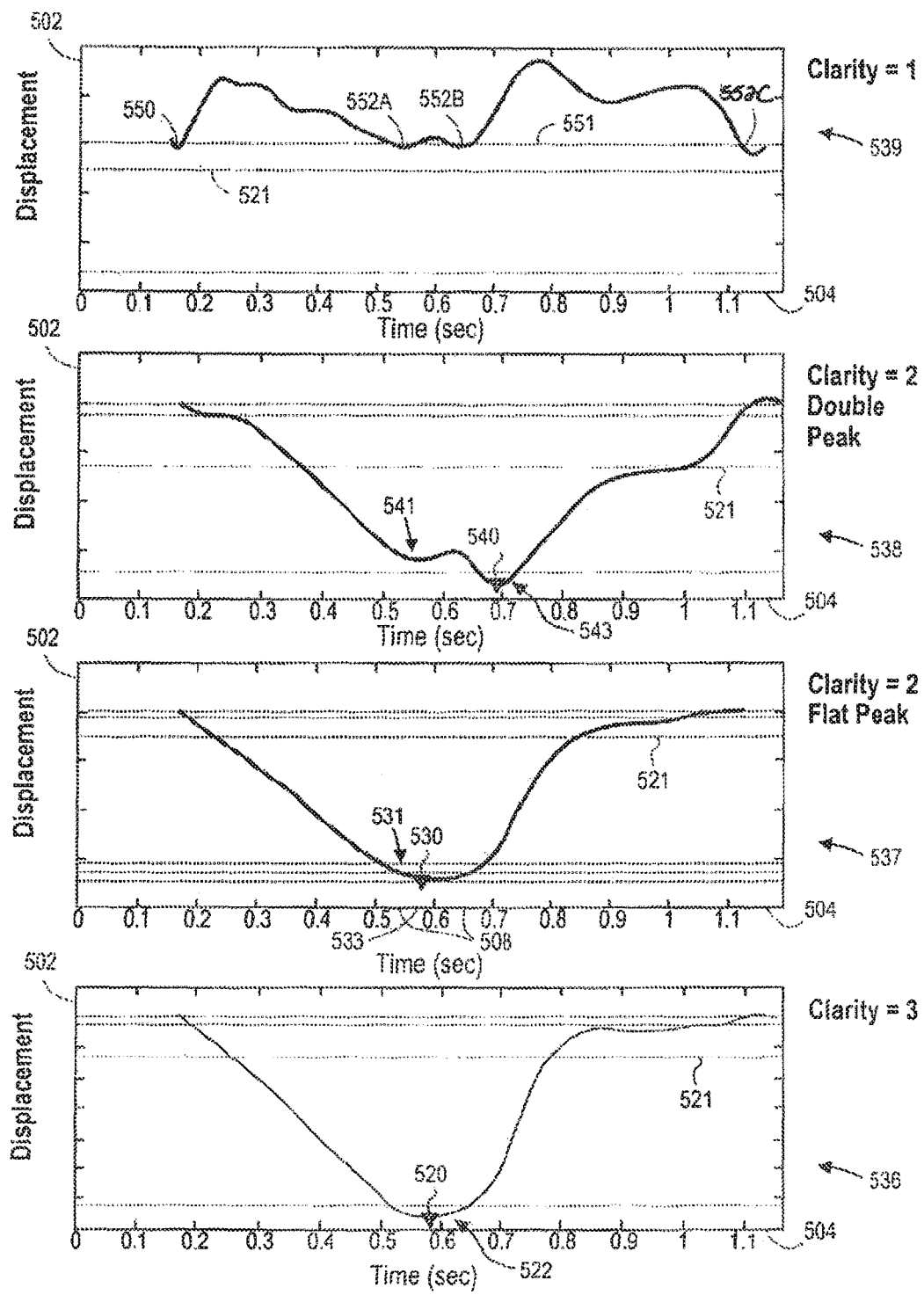
FIG. 5 illustrates motion waveforms at different map points during a single cardiac cycle with corresponding clarity scores in accordance with an embodiment herein.

FIG. 5 illustrates motion waveforms 536-539 defined from PS data points measured at different map points (e.g., the map points 308, 309, 310) during a single cardiac cycle in accordance with an embodiment herein. The motion waveform 536-539 plots radial displacement (e.g., in millimeters) of the map point of interest each along a vertical axis 502 and time along a horizontal axis 504. Each of the map points have a calculated MAT 520, 530, 540, 550 with a corresponding clarity score. The clarity score may be a numerical number representing a predetermined level of confidence in the corresponding MAT of the map point. For example, clarity scores may range from a clarity score of 1 through 3. A clarity score of 1 indicates that there is a low confidence level in the MAT value calculated for the map point. A clarity score of 2 indicates that there is a medium confidence level in the MAT calculated for the map point, but the MAT may be verified or corrected based one or more other map points or calculated MATs. A clarity score of 3 indicates that there is a high confidence level in the MAT value calculated for the map point. It should be noted, that alternative embodiments may have more than or fewer than three levels of clarity scores for the calculated MATs.

The MAT 520 is shown having a clarity score of 3. As described above, the clarity score of 3 may indicate that the ECU 226 has assigned a high confidence in the MAT 520 calculated for the map point. The confidence level of the MAT 520 is based on the distinctive feature of the motion waveform 536, for example, due to the number of peaks of the motion waveform 536. The number of peaks may be determined by the ECU 226 as the number of peaks below a predetermined threshold 521. Additionally or alternatively, the ECU 226 may determine the number of peaks as the number of occurrences, at which the motion waveform 536 has a slope of zero or is parallel to the horizontal axis 504 and falls below the predetermined threshold 521. The motion waveform 536 has a single peak or vertex 522, which has a slope of zero, surrounded by PS motion data points with opposing slopes representing a set minimum displacement for the motion waveform 536.

The MAT 530 is shown having a clarity score of 2. As described above, the clarity score of 2 may indicate that the ECU 226 has assigned a medium confidence in the MAT 530 calculated for the map point. The confidence level of the MAT 530 is based on a feature of the motion waveform 537 that has average distinctiveness, for example, due to the flatness of a peak 531. The distinctiveness of a feature of interest is reduced when the motion wave form includes clouding components, such as flatness, extra peaks and the like. As described above, the ECU 226 may determine the number of peaks, peak 531, as the number of peaks or number of occurrences of zero slope that are below the predetermined threshold 521. The motion waveform 537 is illustrated with one peak, the peak 531. The ECU 226 may determine the flatness of the peak 531 by monitoring displacement values of the PS motion data within the peak 531. The ECU 226 may determine a time period 508 of which the peak 531 or the displacement values of the PS motion data remains within a predetermined displacement range 532. The time period 508 may be compared with a predetermined peak period 533. If the time period 508 is larger than the predetermined peak period 533, as shown in FIG. 5, the peak 531 is flat and an imperfect distinctive feature of the motion waveform 537. Alternatively, if the time period 508 is smaller than the predetermined peak period 533, the peak 531 would be a determined sharp or not flat.

The MAT 540 is shown having a clarity score of 2. The clarity score of the MAT 540 is based on a feature of the motion waveform 538 that has average distinctiveness, for example, due to the number of peaks of the motion waveform 538. As described above, ECU 226 may determine the number of peaks as the number of peaks below the predetermined threshold 521. The motion waveform 538 has two peaks below the predetermined threshold 521, the peaks 541 and 543, which affords as medium distinctive feature.

The MAT 550 is shown having a clarity score of 1. The clarity score of the MAT 550 is based on the lack of a distinctive feature of the motion waveform 539. The motion waveform 539 has no peaks below the predetermined threshold 521. Further, the motion waveform is not line symmetric. For example, at the calculated MAT 550 the PS motion data point is at a displacement value 561. The motion waveform 539 as more than one other PS motion data point 552a-c at the displacement value 551.

Figure 6:
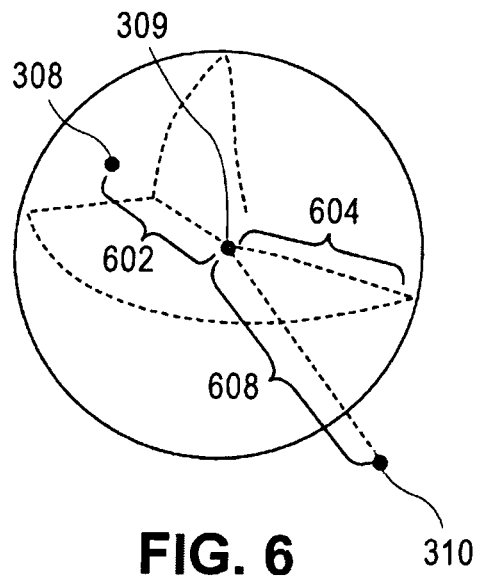
FIG. 6 illustrates map points and a predetermined radius defining a group of neighboring map points in accordance with an embodiment herein.

Returning to FIG. 1, at 106, the method 100 identifies a group of neighboring map points (e.g., the map points 308-310) for a current map point (e.g., the map point 309). Optionally, the group of neighboring map points (e.g., the map points 308-310) may be any map point that is within a predetermined radius 604 (also referred to as neighborhood limit) from the current map point (e.g., the map point 309). For example, the map point 309 may be designated as the current map point and as illustrated in FIG. 6, centered within the predetermined radius 604. The predetermined radius 604 may be 7 mm, such that, any map point outside the predetermined radius 604 or have a distance greater than the predetermined radius 604 from the current map point is excluded from the group of the neighboring map points. The current map point and the predetermined radius 604 may be designated by the user via the operator system interlace 254.

The ECC 226 may calculate a three-dimension (3D) physical distance between pairs of the map points such as between the current map point 309 and another map point 308 and 310 (FIG. 3) using the 3D distance formula of equation 1 below.

$$3D\ Distance = \sqrt{(x_1-x_2)^2 + (y_1-y_2)^2 + (z_1-z_2)^2}$$ (Equation 1)

The cartesian coordinates (e.g., (X, Y, Z)) of each map point 308, 309, and 310 may be determined by the navigation system 220, as described above, by measuring the position of the electrophysiological sensors 252. For example, the map point 309 may be positioned at coordinate (2, 5, 6), the map point 308 may be positioned at coordinate (1, 2, 2), and the map point 310 may be positioned at coordinate (4, 9, 12). The ECC 226 may determine a distance 602 and 608 between the map point 309 and the map points 308 and 310, respectively, using equation 1. For example, 1, the ECC 266 may calculate the distance 602 to be approximately 5.1 mm and the distance 608 to be approximately 7.48 mm. The ECC 266 then will only use the group of neighboring map points 308 and 309. The map point 310 will be excluded from the group of neighboring map points. It should be noted, that the distance to and number of map points will vary.

Optionally, the predetermined radius 604 may vary depending on the location of the current map point. For example, the predetermined radius 604 may be smaller with a current map point at an apical point of the left ventricular relative to a current map point at a basal point of the left ventricular.

Optionally, the predetermined radius 604 may be the radial distance or a proportion of the radial distance from the current map point to a select point on the heart such as the central axis between the apex and the mitral annulus of the left ventricular. Additionally or alternatively, the predetermined radius 604 may be based on a percentage of the surface area of the heart or a portion of the heart, such as the left ventricular, or percentage of the distance from the apex to the mitral annulus measured at a certain point in time.

Figure 7:
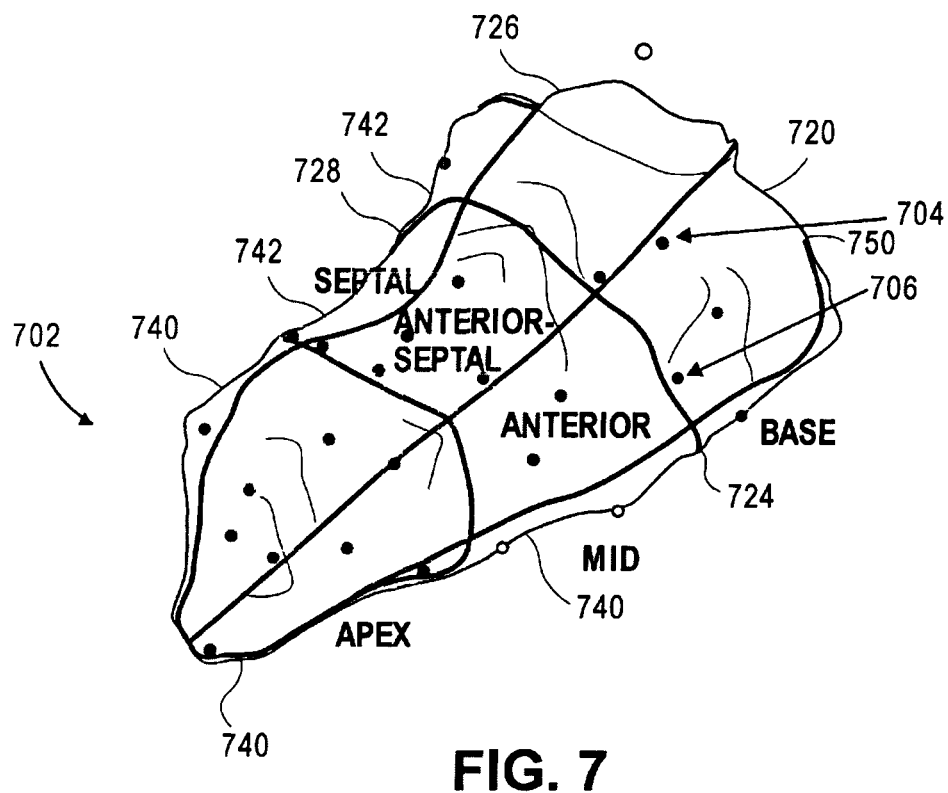
FIG. 7 illustrates map points on the wall of a segmented left ventricalar in accordance with an embodiment herein.

Optionally, the group of neighboring map points may be limited based on predefined segments of the heart wall. FIG. 7 illustrates a left ventricle 702 of the heart divided into 18 segments (not all segments shown) formed from 6 circumferential divisions 740 (not all divisions shown) and 3 longitudinally divisions 742. A current map point 706 may be at a selected position within segment 720. The group of neighboring map points may be any map point positioned within the segment 720. Additionally or alternatively, the group of neighboring map points may be defined as any map point within segment 720 and map points within segments (e.g., segments 724-728) that are adjacent to the segment 720. Additionally or alternatively, map points may be excluded from the group of neighboring map points when a non-tissue area exists between the potential neighbor map points and the current map point 706. For example, if a blood pool 750 separates the current map point 706 from the potential neighbor map point 704, the map point 704 would not be included within the group of neighboring map points (even though the map point 704 is within the segment 720). Additionally or alternatively, map points may be excluded from the group of neighboring map points when other structures are located between the map points that cause the map points to move relatively independently even during normal cardiac motion.

Figure 8:
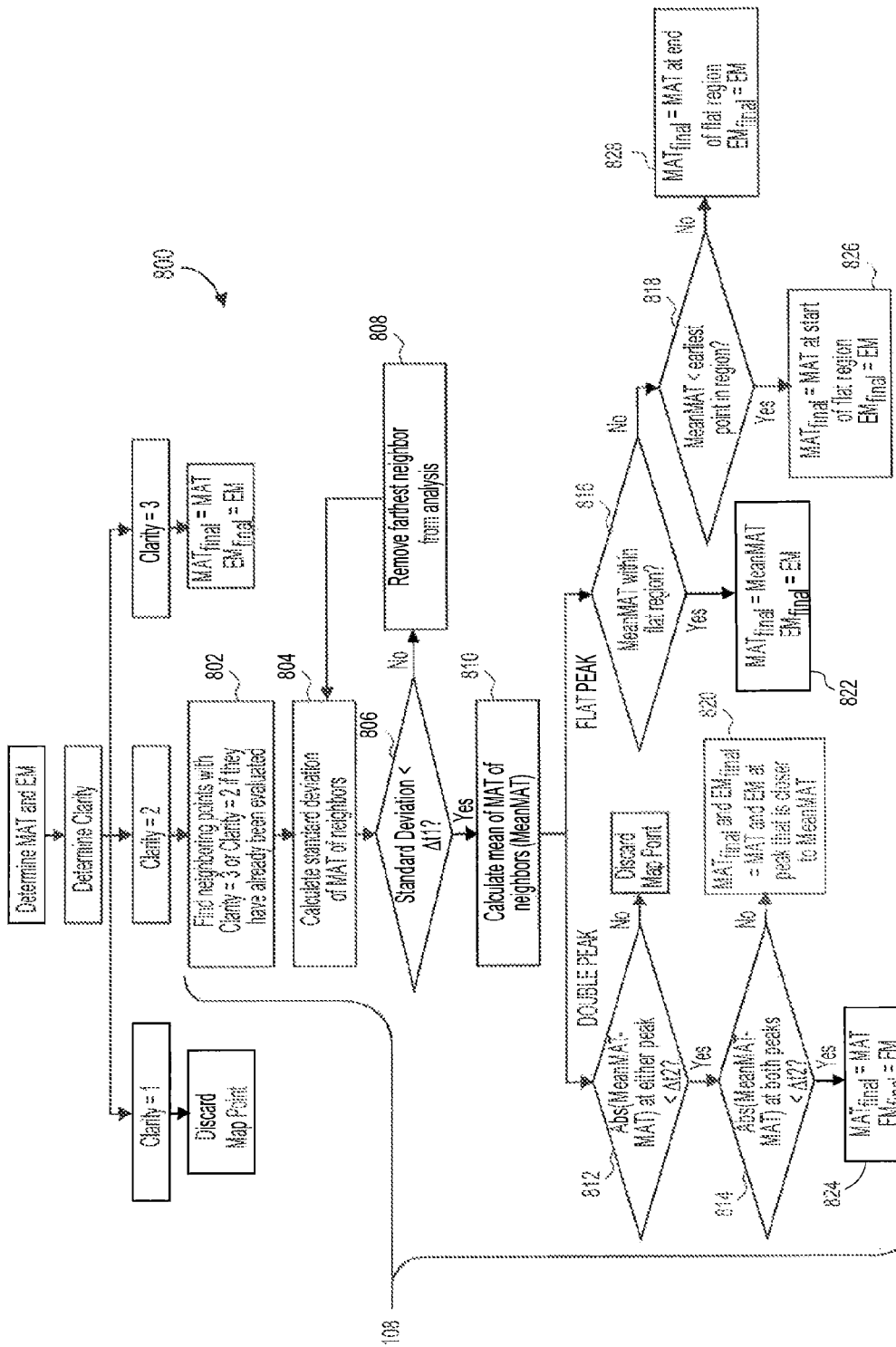
FIG. 8 illustrates motion waveforms at different map points during a single cardiac cycle with corresponding clarity scores in accordance with an embodiment herein.

At 108, the method 100 modifies an MAT 916 corresponding to a current map point 902 based on the calculated MATs 918-924 corresponding to at least a portion of the group of neighboring map points in real-time or prior to implementation of FIG. 1. FIG. 8 illustrates a flow chart of a method 800 for modifying the MAT 916 in accordance with an embodiment based on the calculated MATs 918-924.

Figure 9:
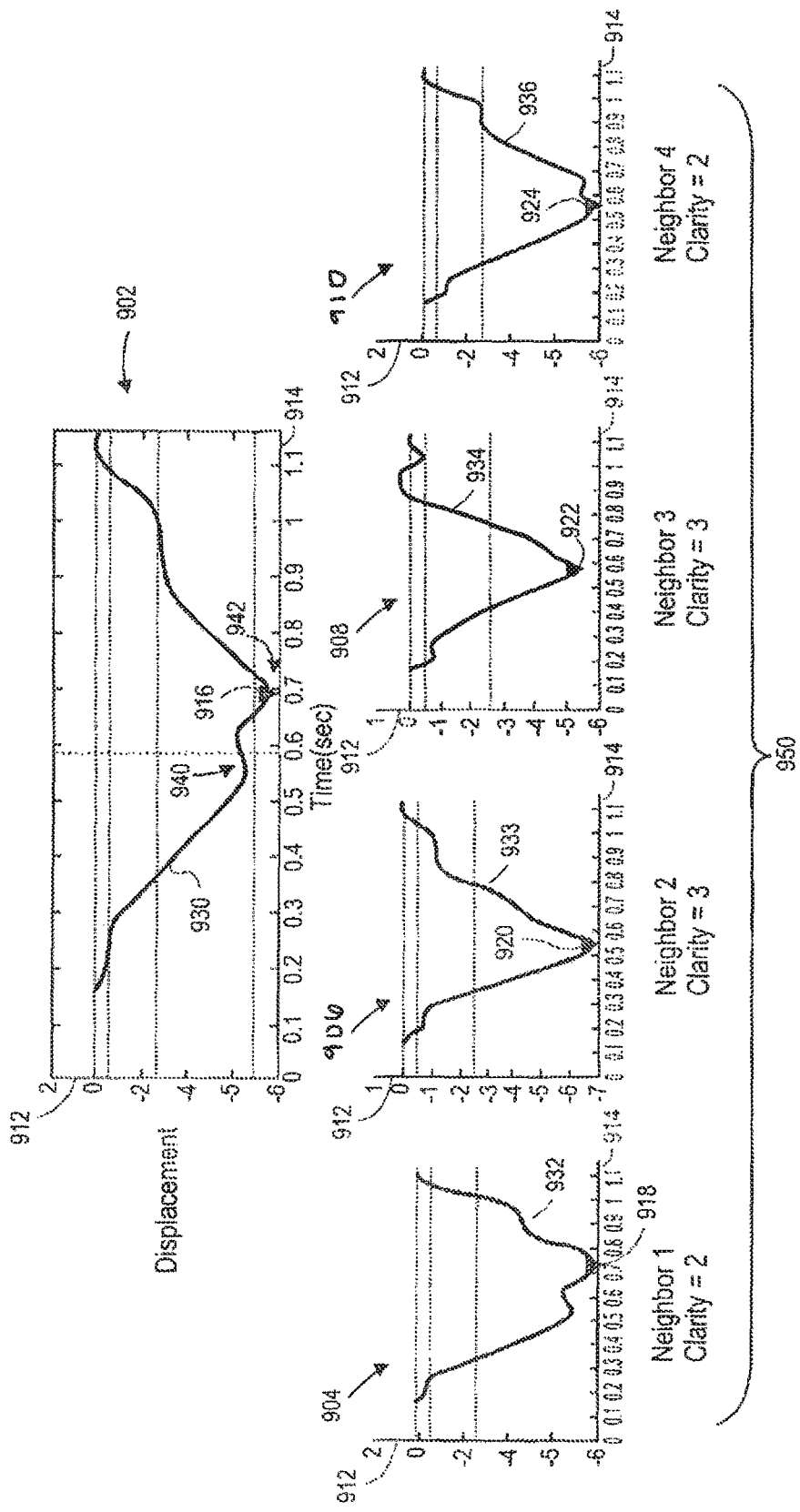
FIG. 9 illustrates a flow chart of a method for characterizing motion data collected by a cardiovascular navigation system, in accordance with an embodiment herein.

At 802, the method 800 selects a portion or a subset of the map points 906-910 from a group of neighboring map points 950, specifically, selecting only map points with a clarity score of 3 (e.g., the map points 906-908 and/or a clarity score of 2 with a re-evaluated MAT (e.g., the map point 910). Map points with a clarity score of 1 and clarity score of 2 without re-evaluation MAT (e.g., the map point 904) are excluded from the portion or subset. FIG. 9 illustrates the motion waveforms 930-936 that are defined from PS data points measured at different map points 902-910 during a single cardiac cycle in accordance with an embodiment herein. The motion waveforms 930-936 plots radial displacement (e.g., in millimeters) of the map points 902-910 of interest on a graph having displacement along a vertical axis 912 and time along a horizontal axis 914.

At 804, the method 800 calculates a standard deviation of the calculated MATs 920-924 for the map points 906-910 from the group of neighboring map points 950. At 806, if the standard deviation of the calculated MATs 920-924 is not within a predetermined threshold Δt1, the method removes the farthest map point neighbor (e.g., the map point 910) from the portion or subset and recalculates the standard deviation of the MAT's for the remaining map points (e.g., the map points 906-908).

If the standard deviation of the calculated MATs 920-924 from the portion of the map points 906-910 is within the predetermined threshold $\Delta t1$, at 808, the method at 810 calculates a mean or MeanMAT of the MATs 920-924. Optionally, the mean or average may be a weighted mean based on a distance of each of the map points 906-910 within the subset from the current map point 902. Optionally, a map point closest to the current map point 902 will be weighted more than a map point further away, relatively, from the current map point 902.

The modification of the MAT 916 may be based on the deviations from the distinctive feature or the unclear motion waveform morphology of the motion waveform 930, such as, a motion waveform with multiple peaks or a flat peak. At 812 and 814, for the motion waveform 930 includes multiple peaks 940 and 942, the MeanMAT is compared with either of the peaks 940 and 942. If neither peak 940, 942 is within a predetermined period $\Delta t2$ of the MeanMAT the map point is discarded. If one of the peaks 940, 942 is within the predetermined period $\Delta t2$, then, at 820, the one peak is set as the MAT for the map point 902. If both peaks 940 and 942 are within the predetermined period $\Delta t2$ then, at 824, the peak 940, 942 closest to the MeanMAT is set as the MAT for the map point 902.

At 816, for a motion waveform with a flat peak (e.g., the motion waveform 537), if the MeanMAT is within the flat region (e.g., the time period 508) the MAT 916 is shifted to MeanMAT (at 822). At 818, determine if the MeanMAT is before an earliest part of the flat region, if so, then at 826 the MAT is shifted to the start of the flat region. If not, then at 828, the MAT of the motion waveform (e.g., the motion waveform 537) is shifted to the end of the flat region.

At 110, the method 100 repeats the identifying and modifying operations for at least a subset of the map points (e.g., the map point 310). For example, an alternative current map point is selected and the operation at 106 and 108 is repeated with the alternative current map point.

Optionally, the CNS 210 (FIG. 2) may also include an imaging system 218. The CNS 210 may further include a registration system for registering a group of images of the anatomical region of the patient 212 in a navigation coordinate system of the medical device navigation system 220 as generally described and shown in U.S. Patent Publication 2013/0272592 and International Pub. No. WO 2012090148, the entire disclosure of which is expressly incorporated herein by reference.

The imaging system 218 may be provided to acquire images of heart 214 or another anatomical region of interest. The imaging system 210 may, for example, comprise of a fluoroscopic imaging system. Additionally or alternatively, rather than a fluoroscopic imaging system, computed tomography (CT) imaging systems, a three-dimensional radio angiography (3DRA) system, and the like may be used. Although the imaging system 218 is described herein for an exemplary embodiment of the invention, the imaging system 218 is not required for the inventive subject matter described within this application The imaging system 218 may include a C-arm support structure 228, a radiation emitter 230, and a radiation detector 232. The emitter 230 and detector 232 are disposed on opposite ends of the support structure 228 and disposed on opposite sides of the patient 212 as the patient 212 lays on an operation table 234. The emitter 230 and detector 232 define a field of view 236 and are positioned such that the field of view 236 includes the anatomical region of interest as the patient 212 lays on the operation table 234. The imaging system 218 is configured to capture images of anatomical features and other objects within the field of view 236. The support structure 228 may have freedom to rotate about the patient 212 as shown by lines 238 and 240. The support structure 228 may also have freedom to slide along lines 242 and 244 (e.g., along the cranio-caudal axis of the patient 212) and/or along lines 246 and 248 (e.g., perpendicular to the cranio-caudal axis of the patient 212). Rotational and translational movement of the support structure 228 yields corresponding rotational and translational movement of the field of view 236.

The imaging system 218 may acquire a group of images of an anatomical region of the patient 212 by first shifting along lines 242, 244, 246, and/or 248 to place the anatomical region of interest within the field of view 236. Second, the support structure 228 may rotate the radiation emitter 230 and the radiation detector 232 about the patient 212, keeping the anatomical region within the field of view 236. The imaging system 218 may capture images of the anatomical region as the support structure 228 rotates, providing a group of two-dimensional images of the anatomical region from a variety of angles. The group of images may be communicated to the ECU 226 for image processing and display. The group of images may comprise a sequence of images taken over a predetermined time period.

Additionally, one or more patient reference sensors (not shown) may be on the body of the patient 212, for example, on the chest. The patient reference sensors measure a displacement and orientation of the patient reference sensors relative to a predetermined reference point, such as, the electrophysiological sensors 252 or the transmitter assembly 250.

Figure 10:
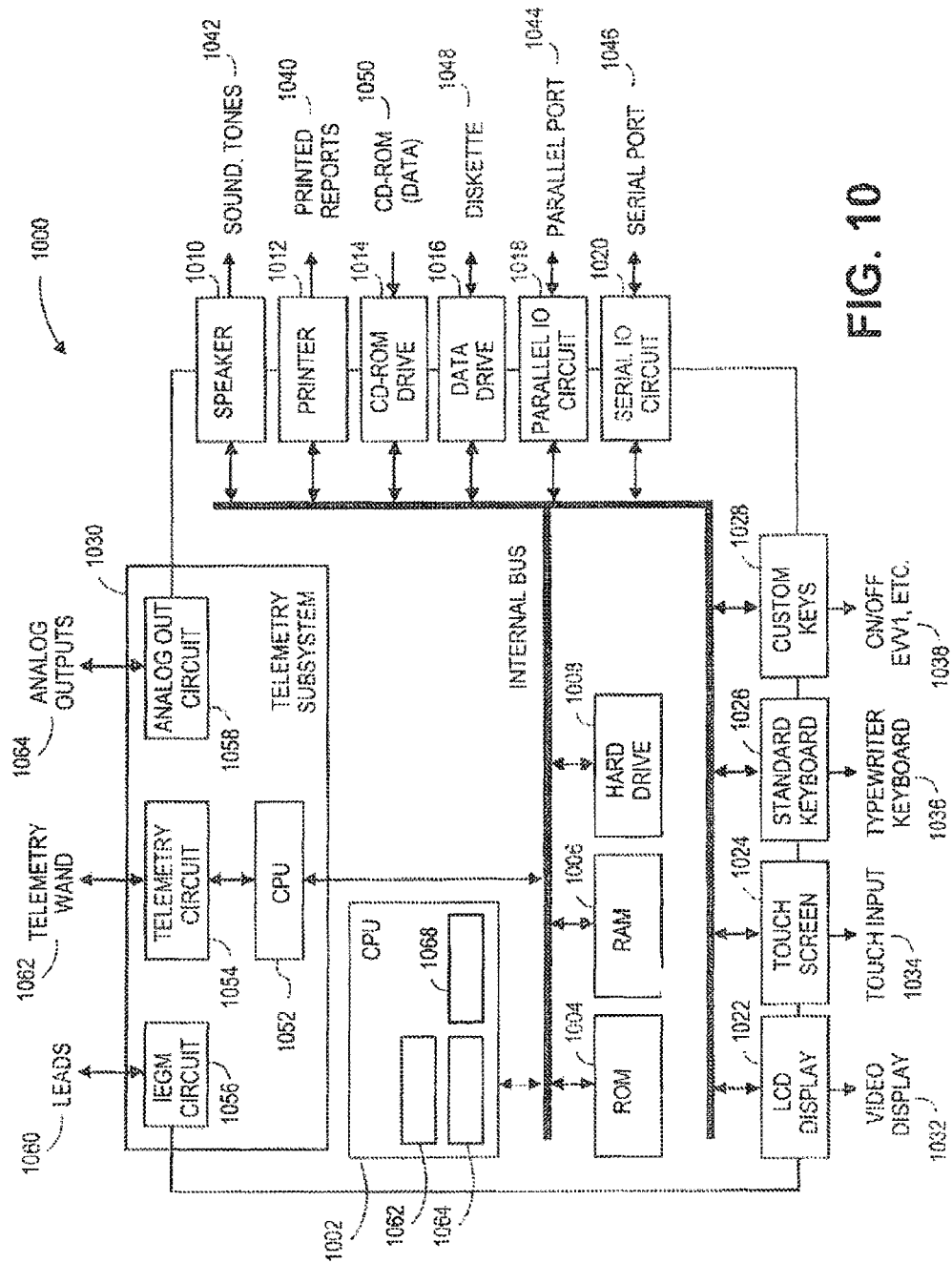
FIG. 10 illustrates a system for analyzing motion data in accordance with an embodiment.

FIG. 10 illustrates a functional block diagram of an embodiment of an electronic control unit (ECU) 1000 that is operated in accordance with the processes described herein to analyze motion data and to interface with the CNS 210. The ECU 1000 may be a workstation, a portable computer, a PDA, a cell phone and the like. The ECU 1000 includes an internal bus that connects/interfaces with a Central Processing Unit (CPU) 1002, ROM 1004, RAM 1006, a hard drive 1008, the speaker 1010, a printer 1012, a CD-ROM drive 1014, a floppy drive 1016, a parallel I/O circuit 1018, a serial I/O circuit 1020, the display 1022, a touch screen 1024, a standard keyboard connection 1026, custom keys 1028, and a telemetry subsystem 1030. The internal bus is an address/data bus that transfers information between the various components described herein. The hard drive 1008 may store operational programs as well as data, such as waveform templates and detection thresholds.

The CPU 1002 typically includes a microprocessor, a microcontroller, or equivalent control circuitry, and may interface with the CNS 210. The CPU 1002 may include RAM or ROM memory, logic and timing circuitry, state machine circuitry, and I/O circuitry to interface with the CNS 210. The display 1022 (e.g., may be connected to the video display 1032). The touch screen 1024 may display graphic information relating to the CNS 210. The display 1022 displays various information related to the processes described herein. The touch screen 1024 accepts a user's touch input 1034 when selections are made. The keyboard 1026 (e.g., a typewriter keyboard 1036) allows the user to enter data to the displayed fields, as well as interface with the telemetry subsystem 1030. Furthermore, custom keys 1028 turn on/off 1038 (e.g., EVVI) the ECU 1000. The printer 1012 prints copies of reports 1040 for a physician to review or to be placed in a patient file, and speaker 1010 provides an audible warning (e.g., sounds and tones 1042) to the user. The parallel I/O circuit 1018 interfaces with a parallel port 1044. The serial I/O circuit 1020 interfaces with a serial port 1046. The floppy drive 1016 accepts diskettes 1048. Optionally, the floppy drive 1016 may include a USB port or other interface capable of communicating with a USB device such as a memory stick. The CD-ROM drive 1014 accepts CD ROMs 1050.

The CPU 1002 is configured to analyze PS motion data collected by the CNS 210 for a plurality of map points to determine a MAT for the map points. The CPU 1002 includes a PS motion data analysis circuit module 1062 that may calculate the MAT as explained herein. Further, the circuit module 1062 may determine the distinctive features of the motion waveform defined by the PS motion data. For example, the circuit module 1062 may determine the number of peaks, flatness, and the slop of the motion waveform defined by the PS motion data that corresponds to a tmap point on the wall of the heart during at least one cardiac cycle. The CPU 1002 includes a MAT analysis circuit module 1064 that is configured to analyze the MAT calculation in relation to the circuit module 1062 to determine a clarity score for the calculated MATs.

A MAT modification circuit module 1068 may identify a group of neighboring map points for a current map point and modify the current map point based on the MAT corresponding to at least a portion of the group of neighboring map points. Optionally, the MAT modification circuit module 1068 may calculate a standard deviation for the neighboring map points.

As one example, the measure circuit module 1068 may determine, as the measure of dyssynchrony, a proportion of the map points that are moving in the select direction which represents at least one of inward during a systole phase and outward during a diastole phase. As another example, the measure circuit module 1068 may calculate, as the measure, a proportion of a number of map points that move in the select direction out of a total number of map points.

The display 1022 displays a dyssynchrony score based on the measure of dyssynchrony in connection with at least one of lead placement for a cardiac resynchronization therapy (CRT) device or programming optimization for a CRT device.

The telemetry subsystem 1030 includes a central processing unit (CPU) 1052 in electrical communication with a telemetry circuit 1054, which communicates with both an IEGM circuit 1056 and an analog out circuit 1058. The circuit 1056 may be connected to leads 1060. The circuit 1056 may also be connected to implantable leads to receive and process IEGM cardiac signals. Optionally, the IEGM cardiac signals sensed by the leads may be collected by the CNS 210 and then transmitted, to the ECU 1000, wirelessly to the telemetry subsystem 1030 input.

The telemetry circuit 1054 is connected to a telemetry wand 1062. The analog out circuit 1058 includes communication circuits to communicate with analog outputs 1064. The ECU 1000 may wirelessly communicate with the CNS 210 and utilize protocols, such as BLUETOOTH™ protocol, GSM™ protocol, infrared wireless LANs, HIPERLAN, 3G, satellite, as well as circuit and packet data protocols, and the like. Alternatively, a hard-wired connection may be used to connect the ECU 1000 to the CNS 210.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hard-wired to perform the methods or portions of the methods described herein, and/or when the processors (e.g., of the devices described herein) operate according to one or more software programs that are written by one or more persons of ordinary skill in the art to perform the operations described in connection with the methods.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein," Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase means for followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

The invention claimed is:

1. A method for characterizing motion data collected by a cardiovascular navigation system, the method comprising:
    obtaining point specific (PS) motion data for a plurality of map points, wherein the PS motion data indicates an amount of motion that occurred at the corresponding map point on a wall of the heart during at least one cardiac cycle;
    calculating mechanical activation times (MAT) for the map points based on the PS motion data;
    identifying a group of neighboring map points for a current map point;
    modifying the MAT corresponding to the current map point based on the MATs corresponding to at least a portion of the group of neighboring map points; and
    repeating the identifying and modifying operations for at least a subset of the map points.

2. The method of claim 1, wherein the calculating operation comprises calculating a three-dimension (3D) physical distance between pairs of map points.

3. The method of claim 1, wherein the PS motion data defines a motion waveform at the corresponding map point, where the motion waveform represents at least one of displacement, strain, or strain rate over a select period of time, the calculating operation calculating the MATs based on the motion waveforms.

4. The method of claim 3, further comprising assigning clarity scores to each of the motion waveforms based on a distinctiveness of a feature of interest within the motion waveforms used to determine the MATs, the clarity scores representing confidence levels in the corresponding MATs.

5. The method of claim 4, wherein the assigning operation assigns the clarity scores based on at least one of a number of peaks, flatness, and a number of zero slopes in the motion waveform.

6. The method of claim 1, further comprising assigning clarity scores to the MATs associated with the map points, wherein the modifying operation determines whether to modify the MAT based on whether the corresponding clarity scores are above a select level.

7. The method of claim 6, wherein, when a first map point has a corresponding clarity above a select first level indicative of a clear motion waveform morphology, a MAT associated with the first map point is not modified based on MATs for the corresponding neighboring map points.

8. The method of claim 6, wherein, when a second map point has a corresponding clarity below a select second level indicative of an unclear motion waveform morphology, a MAT associated with the second map point is modified based on MATs for the corresponding neighboring map points that have higher clarity relative to the clarity of the second map point.

9. The method of claim 6, wherein, when a third map point has a corresponding clarity below a select third level indicative of an unclear motion waveform morphology, a MAT associated with the third map point is discarded and excluded from analysis.

10. The method of claim 1, wherein the identifying operation excludes from the group of the neighboring map points any map points that are further than a predetermined radius away from the current map point.

11. The method of claim 1, further comprising calculating extents of motion (EMs) for the corresponding map points.

12. The method of claim 11, further comprising assigning clarity scores to the MATs and the EMs associated with the corresponding map points.

13. A system for characterizing motion data collected by cardiovascular navigation system (CNS), the system comprising:
    a plurality of physiological sensors configured to be positioned adjacent to a plurality of map points on a heart, wherein the physiological sensors acquire point specific (PS) motion data at the corresponding map points, the PS motion data indicates an amount of motion that occurred at the map points on a wall of the heart during at least one cardiac cycle;
    a PS motion data analysis circuit module configured to determine, from the PS motion data and from the map points, a mechanical activation time (MAT); and
    a MAT modification circuit module configured to modify the MAT of a selected map point based on the MATs corresponding to at least a subset of the map points.

14. The system of claim 13, wherein the PS motion data defines a motion waveform at the corresponding map point, where the motion waveform represents at least one of a displacement, strain, or strain rate over a select period of time, the calculating operation calculating the MATs based on the motion waveforms.

15. The system of claim 14, further comprising a MAT analysis circuit configured to assign a clarity score to the motion waveform based on a distinctiveness of a feature of interest within the motion waveforms used to determine the MATs and at least one of a number of peaks, flatness, and a number of zero slopes in the motion waveform.

16. The system of claim 13, further comprising a MAT analysis circuit configured to assign a clarity score to the calculated MATs, wherein the MAT modification circuit module is configured to modify the MAT of a selected map point based on whether the corresponding clarity scores are above a select level.

17. The system of claim 13, wherein the subset of the map points are within a predetermined radius of the selected map point.

18. The system of claim 17, wherein the subset of the map points and the select map point does not include map points having a corresponding clarity score below a select third level indicative of an unclear motion waveform morphology.

19. The system of claim 17, wherein the select map point has a corresponding clarity score below a select second level indicative of an unclear motion waveform morphology, the subset of the map points have higher clarity scores relative to the select map point.

20. The system of claim 17, wherein the select map point does not have a corresponding clarity score above a select first level indicative of a clear motion waveform morphology.

* * * * *